United States Patent
Stauffer

(10) Patent No.: US 8,030,530 B2
(45) Date of Patent: Oct. 4, 2011

(54) SWING REACTOR AND PROCESS FOR OXYCHLORINATION

(76) Inventor: John E. Stauffer, Greenwich, CT (US)

( * ) Notice: Subject to any disclaimer, the term of this patent is extended or adjusted under 35 U.S.C. 154(b) by 228 days.

(21) Appl. No.: 12/632,840

(22) Filed: Dec. 8, 2009

(65) Prior Publication Data

US 2010/0087691 A1    Apr. 8, 2010

Related U.S. Application Data

(63) Continuation-in-part of application No. 12/140,317, filed on Jun. 17, 2008, now abandoned.

(51) Int. Cl.
  *C07C 17/15* (2006.01)
(52) U.S. Cl. ........................ 570/243; 570/244
(58) Field of Classification Search .................. 570/243, 570/244
  See application file for complete search history.

(56) References Cited

U.S. PATENT DOCUMENTS

| | | | |
|---|---|---|---|
| 5,750,812 A * | 5/1998 | Cowfer et al. | ................ 570/245 |
| 6,204,418 B1 | 3/2001 | Stauffer | |
| 2006/0149102 A1 | 7/2006 | Voight | |
| 2007/0112235 A1 | 5/2007 | Kramer | |
| 2008/0108856 A1 | 5/2008 | Strebelle | |
| 2008/0214879 A1 | 9/2008 | Strebelle | |

* cited by examiner

*Primary Examiner* — Jafar Parsa

(74) *Attorney, Agent, or Firm* — Young Basile Hanlon & MacFarlane, PC

(57) ABSTRACT

A reactor with swing feeds is provided for oxychlorination. This reactor comprises multiple inlets with controls capable of introducing feed streams sequentially to the reactor. In one configuration, a feed stream comprises a paraffin or olefin hydrocarbon such as methane or ethylene, and a second feed stream comprises oxygen and hydrogen chloride. By segregating these feeds, combustion reactions can be minimized and yields of chlorinated components increased.

6 Claims, 3 Drawing Sheets

SWING REACTOR AND PROCESS FOR OXYCHLORINATION

CROSS-REFERENCE TO RELATED APPLICATION

This application is a continuation-in-part of the co-pending U.S. patent application Ser. No. 12/140,317 filed Jun. 17, 2008.

FIELD OF THE INVENTION

Numerous attempts have been made to oxychlorinate paraffins, but the results have been disappointing. When methane, for example, is reacted with oxygen and hydrogen chloride over a suitable catalyst, methyl chloride and higher chlorinated methane compounds are produced. Unfortunately, under these reaction conditions, a significant amount of methane is burned to carbon monoxide and carbon dioxide.

BACKGROUND

To overcome this difficulty, various approaches have been tried. One strategy has been to identify an improved catalyst that will eliminate or at least reduce combustion. Another approach has been to focus attention on the reactor design. For example, a fluidized bed reactor has reputedly been investigated in order to provide better temperature control and presumably give higher yields of products.

To overcome this difficulty, various approaches have been tried. One strategy has been to identify an improved catalyst that will eliminate or at least reduce combustion. Another approach has been to focus attention on the reactor design. For example, a fluidized bed reactor has reputedly been investigated in order to provide better temperature control and presumably give higher yields of products.

Success in these ventures has proven to be elusive. Therefore, it is an object of the present invention to provide an improved reactor design for the oxychlorination of paraffin and olefin hydrocarbons. This object as well as other features and advantages will be apparent from the following description and the figures that are included.

SUMMARY

The present invention provides for a reactor and method of operation with swing feed to be used in the oxychlorination of paraffin and olefin hydrocarbons. Multiple streams of reactants are fed sequentially to the reactor, which contains an oxychlorination catalyst. Control of the feed streams is attained by actuating valves.

The paraffin hydrocarbon may be methane, propane, butane, ethane or any other alkane of interest. The olefin hydrocarbon may be methylene, ethylene or any other. These compounds may be reacted with hydrogen chloride and oxygen or air. Products may comprise mono-substituted or poly-substituted chlorinated hydrocarbons.

The catalyst employed may comprise salts of copper, iron and rare earths. Also, an alkali metal chloride may be incorporated into the catalyst to increase its activity. These catalyst components are deposited on an inert carrier to provide intimate contact with the gas phase.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1A:
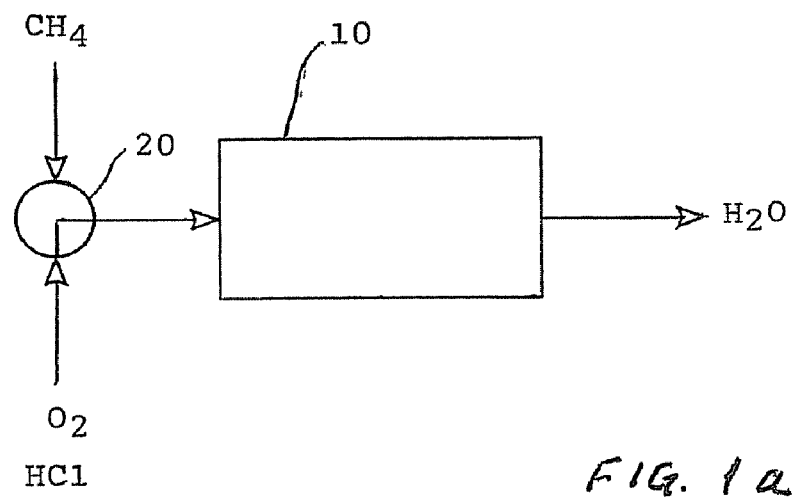
FIGS. 1a and 1b are schematic diagrams of the swing reactor for the case in which two feed streams are employed.

In the prior art, oxychlorination of a hydrocarbon is conducted by feeding a single stream of reactants to a catalytic reactor. Such a single stream will have a uniform composition and contain a given paraffin, hydrogen chloride and oxygen all intimately mixed together.

In contrast to the accepted practice, the present invention contemplates the segregation of the hydrocarbon feed from the oxygen-containing stream. This feature is critical to suppress combustion. The segregation is accomplished by feeding the reactants sequentially in separate streams to the reactor.

Thus, in the specific case where the goal is to chlorinate methane or ethylene, first a stream containing oxygen and hydrogen chloride is fed to the reactor to regenerate the catalyst. After a predetermined time, this stream is turned off and a stream of methane or ethylene is fed to the reactor. Once the catalyst has been depleted of the available chlorine, the methane or ethylene system is shut off, and the cycle is repeated.

The chemistry that takes place during this sequence of events can be shown by the following equations.

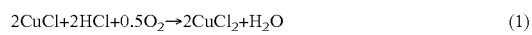

$$2CuCl + 2HCl + 0.5O_2 \rightarrow 2CuCl_2 + H_2O \quad (1)$$

where CuCl is cupric chloride, HCl is hydrogen chloride, $O_2$ is oxygen, $CuCl_2$ is cuprous chloride, and $H_2O$ is water.

$$CH_4 + 2CuCl_2 \rightarrow CH_3Cl + HCl + 2CuCl \quad (2)$$

where $CH_4$ is methane, $CH_3Cl$ is methyl chloride.

The regeneration of the catalyst is shown in equation 1, and the depletion of the catalyst during the chlorination of methane is shown in equation 2.

The chemistry for ethylene is shown by the following equations:

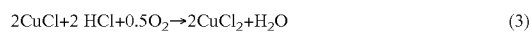

$$2CuCl + 2HCl + 0.5O_2 \rightarrow 2CuCl_2 + H_2O \quad (3)$$

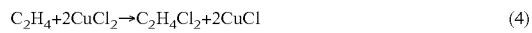

$$C_2H_4 + 2CuCl_2 \rightarrow C_2H_4Cl_2 + 2CuCl \quad (4)$$

In equation (4), $C_2H_4$ is ethylene and $C_2H_4C_2$ is ethylene dichloride. It will be noted that equations (1) and (3) are the same.

The catalyst may contain other active constituents besides copper, but the chemistry is the same. For example, iron chloride may be included for the purpose of depressing the melting point of the catalyst. In this regard, potassium chloride is especially effective.

The reaction temperature must be sufficiently high to overcome the inertness of the alkane to be chlorinated. In the neighborhood of 450° the reaction kinetics are favorable, however, at these temperatures the alkane is subject to combustion. Therefore, the provisions of the present invention are all-important.

Figure 1B:
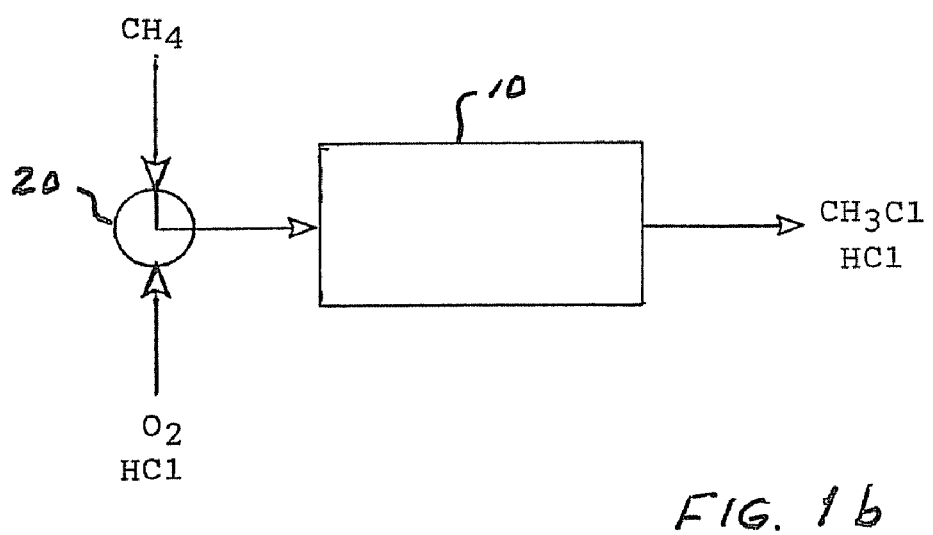

The actual workings of a swing reactor are illustrated in FIG. 1. First, the value 20 is set to provide the reactor 10 with a stream containing oxygen and hydrogen chloride as shown in FIG. 1a. Thereafter, by turning valve 20, the oxygen/hydrogen chloride stream is shut off and a stream of methane is fed to the reactor as shown in drawing FIG. 1b.

Under ideal conditions, there is no mixing between the oxygen containing stream and the methane stream. Such a result can be achieved with plug flow, this condition can be approached by designing the reactor 10 to contain a minimum of dead space and by minimizing back mixing in the catalyst bed.

Figure 2A:
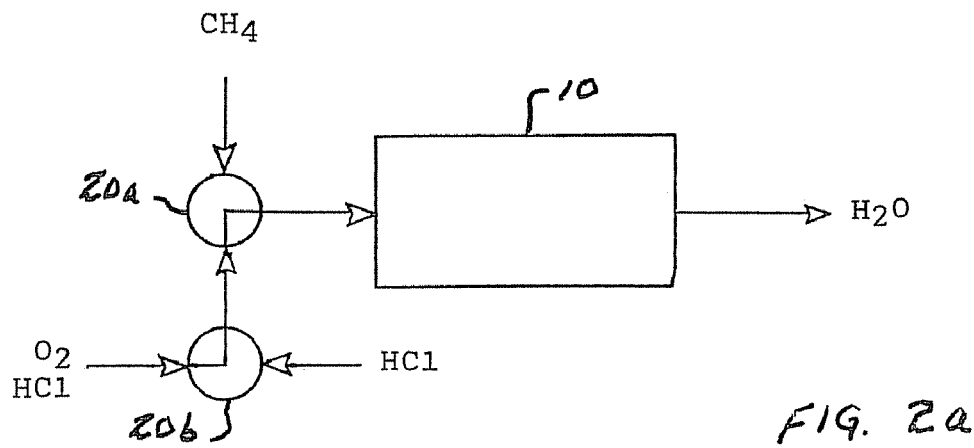
FIGS. 2a, 2b and 2c are schematic diagrams for three feed streams.
Figure 2B:
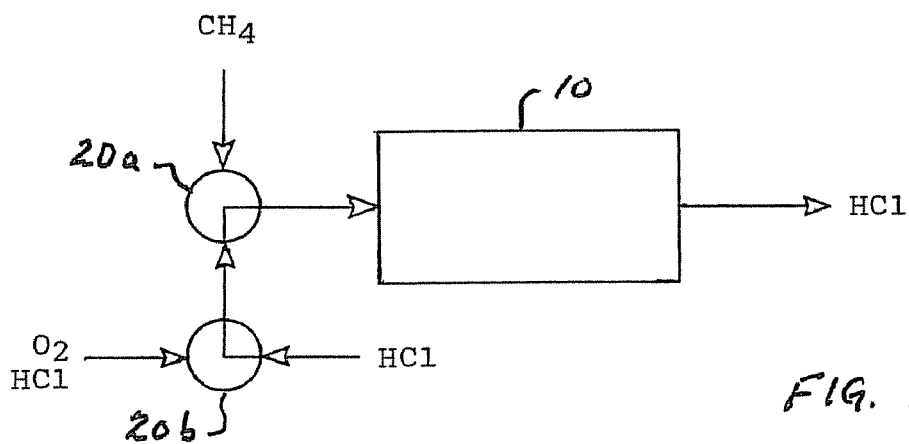
Figure 2C:
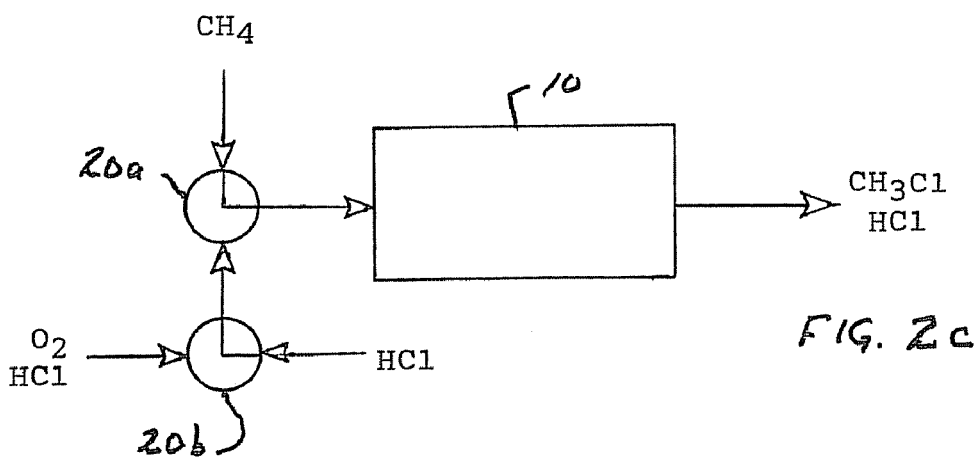

FIGS. 2a, 2b and 2c show an alternative in which the hydrocarbon and oxygen streams are completely segregated. This reactor functions by using three feed streams: FIG. 2c, a methane (or ethylene) stream, FIG. 2a, an oxygen-containing stream, and FIG. 2b, a hydrogen chloride stream. Two valves, 20a and 20b, are required. The different modes of operating are shown in drawings (a), (b) and (c). A complete cycle of operation would contain the following sequence of feeds: oxygen, hydrogen chloride, methane, hydrogen chloride. The sequence then repeats.

Figure 3A:
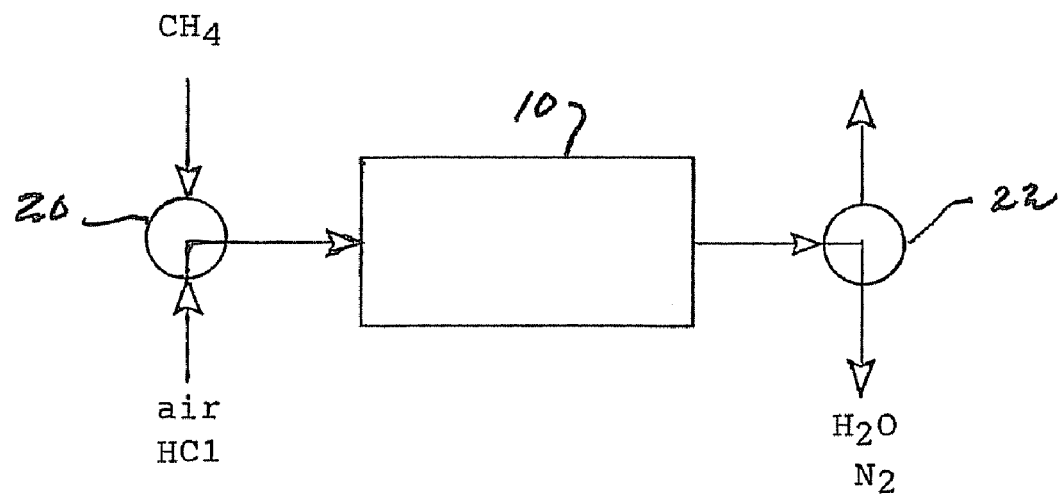
FIGS. 3a and 3b are swing reactor diagrams with two effluent streams.
Figure 3B:
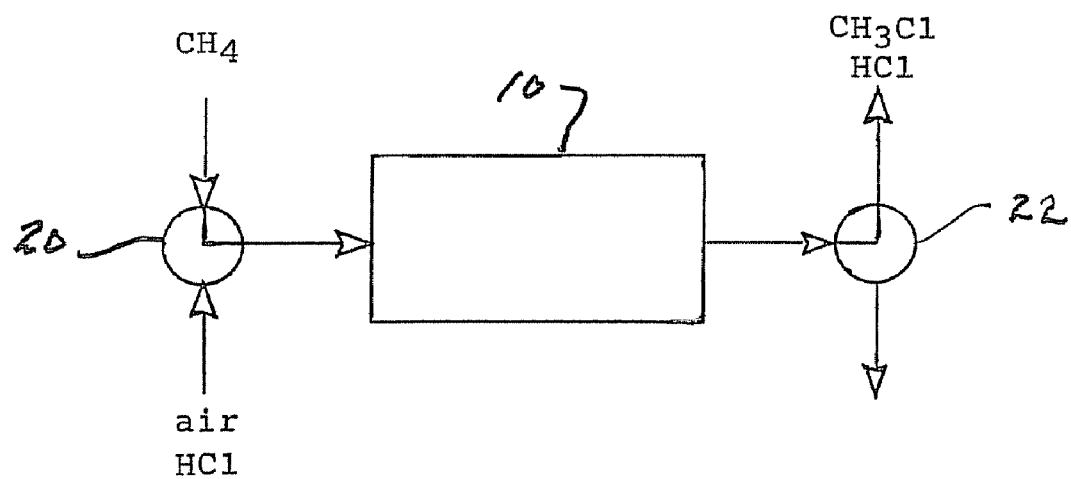

In chlorination processes, an excess of hydrocarbon feed is often employed in order to control the product yields. In these processes, the unreacted hydrocarbon is recovered and recycled to the feed stream. Such a procedure can be accommodated in a swing reactor by providing for two effluent streams as shown in FIGS. 3a and 3b. Using this layout, air can be substituted for oxygen without complicating product recovery.

The input valve 20 is operated as described above with respect to FIGS. 1a and 1b. Air, of course, contains oxygen as well as nitrogen, so the inputs to reactor 10 are essentially the same. An output valve 22 is added. One effluent stream is water and nitrogen while the other is CH3Cl and HCl, depending on the position of the valve.

The dynamics of a swing reactor depends on the relative quantity of catalyst and the flow rates. The cycle frequency can be expressed by the following equation.

$$f = S/M \quad (5)$$

where f is the frequency in cycles per second, S is the flow rate of hydrogen chloride in moles per second, and M is the moles of copper chloride in the catalyst.

Some interesting conclusions can be drawn from the above expression. As the frequency is increased, the quantity of catalyst can be reduced for a given flow rate. Or keeping the catalyst constant, the flow rate can be increased by increasing the frequency.

The present invention represents an effective means of reducing and possibly eliminating combustion reactions during the oxychlorination of paraffin and olefin hydrocarbons. The result is increased yields of product, simplified recovery procedures, and lower capital investment. The flexibility provided by a swing reactor should expand the interest in oxychlorination chemistry.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for the catalytic oxychlorination of a paraffin or olefin hydrocarbon comprising the separately and sequentially performed steps of:
   (a) feeding oxygen into a reactor containing an oxychlorinafion catalyst; and
   (b) feeding a paraffin or olefin hydrocarbon into said reactor wherein said hydrocarbon is an alkane.

2. A method as described in claim 1 wherein the alkane is one of methane, propane or butane.

3. A method as described in claim 1 wherein the catalyst is chosen from the group consisting of salts of copper, iron and rare earths.

4. A method for the catalytic oxychlorination of a paraffin or olefin hydrocarbon carried out in a reactor having an input connected to a valve mechanism having two alternative input conditions which can be separately and independently selected comprising the steps of:
   feeding oxygen into the reactor through the valve mechanism in a first input condition wherein the reactor contains an oxychlorination catalyst; and
   feeding a paraffin or olefin hydrocarbon into said reactor through the valve mechanism in a second input condition.

5. The method of claim 4 in which the reaction is carried out with minimal combustion.

6. The method of claim 4 wherein the reaction is carried out of a temperature of about 450° C.

* * * * *